(12) United States Patent
Weinberg et al.

(10) Patent No.: US 10,034,633 B2
(45) Date of Patent: Jul. 31, 2018

(54) NEUROPARTICLE WITH A SPIN-TORQUE DEVICE

(71) Applicants: WEINBERG MEDICAL PHYSICS LLC, Bethesda, MD (US); UNIVERSITY OF MARYLAND, COLLEGE PARK, College Park, MD (US)

(72) Inventors: Irving N. Weinberg, Bethesda, MD (US); Edo Waks, Washington, DC (US); Benjamin Shapiro, Washington, DC (US)

(73) Assignees: WEINBERG MEDICAL PHYSICS INC., North Bethesda, MD (US); UNIVERSITY OF MARYLAND COLLEGE PARK, College Park, MD (US)

( * ) Notice: Subject to any disclaimer, the term of this patent is extended or adjusted under 35 U.S.C. 154(b) by 781 days.

(21) Appl. No.: 14/632,982

(22) Filed: Feb. 26, 2015

(65) Prior Publication Data

US 2015/0238110 A1     Aug. 27, 2015

Related U.S. Application Data

(63) Continuation-in-part of application No. 14/221,777, filed on Mar. 21, 2014, now Pat. No. 9,622,809.
(Continued)

(51) Int. Cl.
*A61B 5/00* (2006.01)
*H02J 7/02* (2016.01)
(Continued)

(52) U.S. Cl.
CPC .......... *A61B 5/4041* (2013.01); *A61B 5/0515* (2013.01); *H02J 7/025* (2013.01); *H02J 50/00* (2016.02); *H02J 50/10* (2016.02); *A61B 5/065* (2013.01); *A61B 5/6877* (2013.01); *A61B 18/1206* (2013.01);
(Continued)

(58) Field of Classification Search
CPC ..... A61B 5/4041; A61B 5/6877; A61B 5/065; A61B 5/0515; A61B 2560/0219; A61B 2562/0285; A61B 2018/00613; A61B 18/1206; H02J 50/00; H02J 50/10; H02J 7/025; A61N 2005/1098; A61N 1/36014
See application file for complete search history.

(56) References Cited

U.S. PATENT DOCUMENTS

2008/0309330 A1*  12/2008  Ohyu .............. A61B 5/05
                                                324/232
2009/0203988 A1*  8/2009  Phua .............. A61B 5/024
                                                600/409
(Continued)

OTHER PUBLICATIONS

Boland et al.; Micro electret power generator; IEEE Conference on Micro Electro Mechanical Systems; Jan. 19-23, 2003; pp. 538-541.
(Continued)

*Primary Examiner* — Peter Luong
(74) *Attorney, Agent, or Firm* — Barnes & Thornburg LLP

(57) ABSTRACT

Disclosed embodiments enable determining and monitoring the location of at least one particle in a subject's body, as well as the status of a local environment within the body where the at least one particle is located.

41 Claims, 4 Drawing Sheets

Related U.S. Application Data

(60) Provisional application No. 61/945,615, filed on Feb. 27, 2014.

(51) Int. Cl.
    *H02J 50/00*     (2016.01)
    *A61B 5/05*     (2006.01)
    *H02J 50/10*     (2016.01)
    *A61B 18/12*     (2006.01)
    *A61N 1/36*     (2006.01)
    *A61N 5/10*     (2006.01)
    *A61B 18/00*     (2006.01)
    *A61B 5/06*     (2006.01)

(52) U.S. Cl.
    CPC ............ *A61B 2018/00613* (2013.01); *A61B 2560/0219* (2013.01); *A61B 2562/0285* (2013.01); *A61N 1/36014* (2013.01); *A61N 2005/1098* (2013.01)

(56) References Cited

U.S. PATENT DOCUMENTS

| | | | |
|---|---|---|---|
| 2010/0167057 A1* | 7/2010 | Ying | B82Y 30/00 428/402 |
| 2012/0001656 A1 | 1/2012 | Hu et al. | |
| 2013/0257428 A1 | 10/2013 | Weinberg et al. | |
| 2014/0043891 A1 | 2/2014 | Edelstein et al. | |
| 2014/0206927 A1 | 7/2014 | Weinberg | |
| 2014/0309479 A1 | 10/2014 | Weinberg et al. | |

OTHER PUBLICATIONS

Cadwallader; Gallium Safety in the Laboratory; Idaho National Engineering and Environmental Laboratory; 2003.

Cao et al.; Bi-Directional Micro Relays with Liquid-Metal Wetted Contacts; IEEE; 2005; pp. 371-374.

Chen et al.; Thermal and Hydrodynamic Characteristics of Constructual Tree-Shaped Minichannel Heat Sink; 2010; pp. 2018-22029; Vo. 56, No. 8.

Crump; Direct Digital Manufacturing Part One: What is Direct Digital Manufacturing; Fortus 3D Production Systems; 2009.

Cui et al.; Magnetic Force Driven Nanogenerators as a Noncontact Energy Harvester and Sensor; Nano Lett.; 2012; vol. 12, No. 7; pp. 3701-3705.

Dussaux et al.; Large microwave generation from current-driven magnetic vortex oscillators in magnetic tunnel junctions; Nature Communications; Apr. 12, 2010; vol. 1, No. 8.

El-Sharkawy et al.; Absolute Temperature Monitoring Using RF Radiometry in the MRI Scanner; IEEE Transactions on Circuits and Systems; Nov. 2006; vol. 53; Issue 11; pp. 2396-2404.

Fan et al.; Flexible triboelectric generator; Nano Energy; Mar. 2012; vol. 1, Issue 2; pp. 328-334.

Kaka et al.; Mutual phase-locking of microwave spin torque nano-oscillators; Nature; Sep. 15, 2005; vol. 437; pp. 389-392.

Knoblauch et al.; A Galinstan Expansion Femtosyringe for Microinjection of Eukaryotic Organelles and Prokaryotes; Nature Biotechnology; 1999; pp. 906-909; vol. 17.

Kolm; Hydromagnet: A Self-Generating Liquid Conductor Electromagnet; M.I.T. National Magnet Laboratory; 1961; pp. 1296-1304; vol. 32, No. 7.

Morley et al.; The MTOR LM-MHD Flow Facility, and Preliminary Experimental Investigation of Thin-Layer, Liquid Metal Flow in a I/R Toroidal Magnetic Field; Fusion Science and Technology; 2003; pp. 74-78; vol. 44.

Prokopenko et al.; Spin-Torque Nano-Oscillator as a Microwave Signal Source; Magnetics Letters, IEEE; 2011; vol. 2.

Rapaport et al; A Glucose Fuel Cell for Implantable Brain-Machine Interfaces; PlosOne; Jun. 2012; vol. 7; Issue 6.

Redinger et al.; An Ink-Jet-Deposited Passive Component Process for RFID; IEEE; 2004; pp. 1978-1983.

Röck et al.; Electronic Nose: Current Status and Future Trends; Chem. Rev. 2008; vol. 108; pp. 705-725.

Urdaneta et al.; Goodbye Wires and Formers: 3-D Additive Manufacturing and Fractual Cooling Applied to MRI Gradient Coils.

Zeng et al.; Ultralow-current-density and bias-field-free spin-transfer nano-oscillator; Published Mar. 12, 2013; Nature; Scientific Reports 3; Article No. 1426.

U.S. Appl. No. 61/810,436, filed Apr. 10, 2013.

Freitas, PP et al., "Spintronic Platforms for Biomedical Applications", in Lab Chip., 2012, vol. 12, pp. 547, 553, 555, Dec. 7, 2011.

Notification of Transmittal of the International Search Report and the Written Opinion of the International Search Authority, or the Declaration for International Patent Application No. PCT/US2015/017814 dated Feb. 26, 2015.

* cited by examiner

NEUROPARTICLE WITH A SPIN-TORQUE DEVICE

CROSS-REFERENCE TO RELATED APPLICATION(S)

This application relies for priority on U.S. Provisional Patent Application Ser. No. 61/945,615, entitled "Neuroparticle with a spin-torque device," filed on Feb. 27, 2014, and U.S. patent application Ser. No. 14/221,777, entitled Apparatus and Method for Spatially Selective Interventional Neuroparticles," filed Mar. 21, 2014, the entirety of both applications being incorporated by reference herein.

FIELD OF THE INVENTION

Disclosed embodiments are directed, generally, to the use of nano- and micro-engineered electromagnetic devices to report on the anatomy and physiology of internal body organs and systems.

DESCRIPTION OF THE RELATED ART

The spin of an electron is an angular momentum that is separate from the angular momentum due to its orbital motion. Like orbital angular momentum, the spin has an associated magnetic moment. The spins of many electrons can act together to affect the magnetic and electronic properties of a material. A spintronic particle requires manipulation of spin-polarized electrons to generate a net surplus of spin up or spin down electrons.

Spin Torque Nano-Oscillators (STNOs, also known as spin-valves) are one class of spintronic devices. In an STNO, currents of flowing electrons are polarized as a result of interactions with a magnetic layer. The spin-polarized current can then interact with a second magnetic layer, imparting momentum ("spin-torque") that can drive microwave oscillations of the magnetic orientation of this second magnetic layer. These oscillations may be detected using external radiofrequency antennas. For the purpose of this invention description, STNOs are presented as one component of one enabling configuration. It is understood that other spintronic particles (e.g., spin vortex) may be used instead of the STNO, or that the classic STNO may be modified, as part of the invention.

SUMMARY

The following presents a simplified summary in order to provide a basic understanding of some aspects of various invention embodiments. The summary is not an extensive overview of the invention. It is neither intended to identify key or critical elements of the invention nor to delineate the scope of the invention. The following summary merely presents some concepts of the invention in a simplified form as a prelude to the more detailed description below.

Disclosed embodiments enable determining and monitoring the location of at least one particle in a subject's body, as well as the status of a local environment within the body where the at least one particle is located. Disclosed embodiments also enable the ability to affect the local environment in which the particle is located. For example, the particle, once localized through the application of this invention, may affect the local environment through the release of electrical energy from an antenna that is attached to the particle or through the triggered release of chemicals from a reservoir that is attached to or influences by the particle.

In accordance with at least one disclosed embodiment, an apparatus is provided that may be introduced to and be resident in a body, wherein the apparatus includes at least one spin torque nano-oscillator and at least one receiver outside the body, wherein the receiver is sensitive to the radiation emitted by the at least one particle.

In accordance with at least one disclosed embodiment, a method for imaging the neural activity in a body through the use of at least one particle is provided wherein a spin-valve emits electromagnetic radiation that is sensitive to electromagnetic aspects of a local environment associated with neural activity and is also sensitive to electromagnetic gradients applied by one or more generators external to the body.

Disclosed embodiments use nano- and micro-engineered electromagnetic devices to report on the anatomy and/or physiology of internal body organs and systems of a subject.

In illustrative embodiments, the location of a spintronic particle, as well as a status of a local environment of the spintronic particle may be determined.

The term local environment is intended to include the magnetic and/or electric field at the spintronic particle, as well as chemical, biological or mechanical structures within the sensory range of one or more sections of the spintronic particle.

In illustrative embodiments, the particle may also affect the local environment, for example through the release of electrical energy from an antenna or a triggered release of chemicals.

Illustrative embodiments further apply a novel use of spin-torque methods to broadcast information from the spintronic particle to an apparatus located outside the body of the subject.

BRIEF DESCRIPTION OF THE FIGURES

A more complete understanding of the present invention and the utility thereof may be acquired by referring to the following description in consideration of the accompanying drawings, in which like reference numbers indicate like features, and wherein.

DETAILED DESCRIPTION OF THE INVENTION

Figure 1:
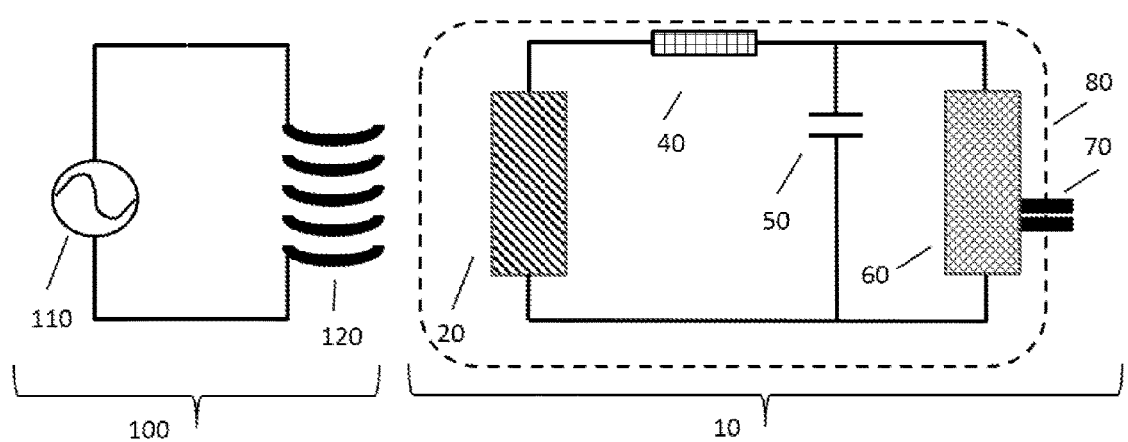
FIG. 1 illustrates, in broad terms, components of an example of an electromagnetic device provided in accordance with a disclosed embodiment.

The description of specific embodiments is not intended to be limiting of the present invention. To the contrary, those skilled in the art should appreciate that there are numerous variations and equivalents that may be employed without departing from the scope of the present invention. Those equivalents and variations are intended to be encompassed by the present invention.

In the following description of various invention embodiments, reference is made to the accompanying drawings, which form a part hereof, and in which is shown, by way of illustration, various embodiments in which the invention may be practiced. It is to be understood that other embodiments may be utilized and structural and functional modifications may be made without departing from the scope and spirit of the present invention.

Moreover, it should be understood that various connections are set forth between elements in the following description; however, these connections in general, and, unless otherwise specified, may be either direct or indirect, either permanent or transitory, and either dedicated or shared, and that this specification is not intended to be limiting in this respect.

Disclosed embodiments enable determining and monitoring the location of at least one particle in a subject's body, as well as the status of a local environment within the body where the at least one particle is located.

Disclosed embodiments also enable the ability to affect the local environment in which the particle is located. For example, the particle may affect the local environment through the release of electrical energy from an antenna or triggered release of chemicals.

In accordance with at least one disclosed embodiment, one or more magnetic gradients may be used to transport the particles within a body, e.g., the body of a subject to be imaged, for example, a human body. This transport would take advantage of the magnetic properties of particle constituents, so that an externally-applied magnetic gradient that would accelerate, translate, and/or rotate the particle. Methods for transporting magnetic particles were disclosed in U.S. patent application Ser. No. 14/182,488, entitled "System, Method and Equipment for Implementing Temporary Diamagnetic Propulsive Focusing Effect with Transient Applied Magnetic Field Pulses" and related applications.

Disclosed embodiments apply a novel use of spin-torque methods to broadcast information from the particle to an apparatus located outside a subject's body.

The term "Spin-Torque Nano Oscillator" (STNO) is conventionally known to refer to a class of small structures that utilize spin valve principles in order to generate electromagnetic radiation. All such small structures may be referred to and encompassed by the term "STNO" or spin-valve for the purposes of this disclosure.

It is conventionally known that noise level in a Magnetic Resonance Imaging (MRI) Radio Frequency (RF) coil is on the order of $10^{-14}$ watts. See the 2006 article by AbdEl-Momen M. El-Sharkawy entitled "Absolute Temperature Monitoring Using RF Radiometry in the MRI Scanner", published in IEEE Trans Circuits Syst. I Regul. Pap., vol. 53(11), pages 2399 (incorporated herein by reference in its entirety).

According to the 2010 scientific article by O. Prokopenko in the journal of Applied Physics Letters, entitled "Spin-torque nano-oscillator as a microwave source" (incorporated herein by reference in its entirety), STNOs can yield power on the order of $10^{-11}$ watts, with the highest powers available when the STNO is surrounded by amplifying structures such as a ring or resonator.

According to the 2005 article by S. Kaka in the journal of Nature, entitled "Mutual phase-locking of microwave spin torque nano-oscillators", multiple STNOs may fire synchronically in order to further boost signal.

It should be understood that the variation of magnetic moment of an STNO is included in the term "electromagnetic radiation" and "Radio Frequency" or "RF" for the purposes of this disclosure.

FIG. 1 illustrates, in broad terms, components of an example of the electromagnetic device 10 that may be introduced into a body. The electromagnetic device 10 may be implemented as a "particle", and may include a spin-torque device 20 which may be connected electrically through resistive and other circuit elements, for example, diodes 40, to an energy storage or production device 50, e.g., a capacitor. Energy from the storage device 50 may be used to power or activate spin-torque device 20.

The electromagnetic device 10 may also include a stimulator circuit 60, which has antennae and/or contacts 70 that can stimulate nearby tissue within the body. Thus, the storage device 50 may also be used to power the stimulator circuit 60.

In accordance with at least one embodiment, the device 10 may be encapsulated by bio-compatible material 80, through which at least some portion of antennae 70 may protrude. Portions of antennae 70 may protrude into extracellular space or may penetrate into cells.

In accordance with at least one embodiment, the electromagnetic device 10 may be introduced into and resident in a body and exposed to an electromagnetic field generated by an apparatus 100 external to the body. Such an external apparatus may include a power supply of modulated current 110, an electromagnetic transmitter coil 120, and a receiver of electromagnetic radiation which may be the same as electromagnetic transmitter coil or antenna 120 or may be a separate coil or antenna (not shown). Energy may be conveyed to the storage device 50 from a fuel-cell or via transfer of energy from the external apparatus 120 to an antenna or another form of energy transducer in the particle, or from a fuel-cell.

Alternatively the spintronic device 20 may not require an external source of energy, and may be powered by electrical currents derived from nearby nerve cells.

Figure 2:
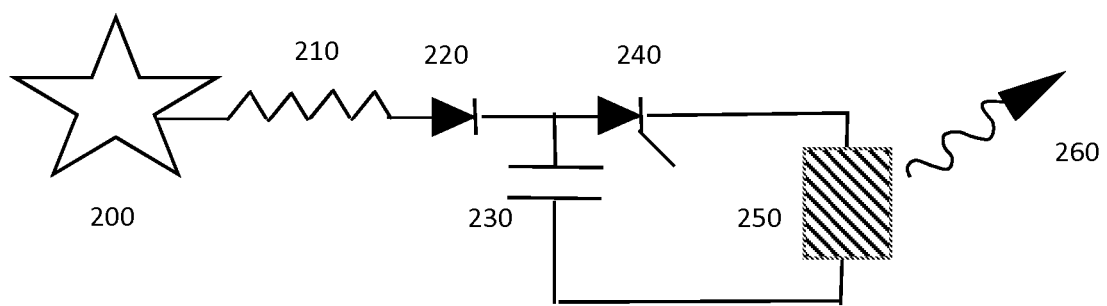
FIG. 2 illustrates one example of a configuration wherein at least one particle is powered by electrical currents derived from nearby nerve cells.

One example of this configuration is illustrated in FIG. 2, where one or more portions of one or more nerve cells 200 are in the vicinity of a conducting path (including resistance 210) and an optional diode 220 in order to deposit charge on capacitor 230. When the voltage on capacitor 230 is above a threshold value, then diode 240 conducts current into spintronic device 250, which emits RF energy 260. It is understood that diode 240 may be a Shockley diode, a dynistor, a silicon controlled rectifier, or some other electronic element that will discharge a capacitor above a certain threshold voltage in order to effectively compress the initial current from the nerve cell into a stronger and shorter current pulse that may activate the spintronic device.

It should further be understood that the receiver of the electromagnetic radiation may be a coil, or may be some other device that is sensitive to electromagnetic radiation (for example, a Super-Conducting QUantum Interference Device, or "SQUID").

It should be understood that the energy storage or production device 50 may be a fuel-cell, for example, such as that disclosed in the 2012 article (volume 12, issue 6) by Rapaport et al. in journal PLOSone, entitled "A Glucose Fuel Cell for Implantable Brain-Machine Interface" (incorporated herein by reference in its entirety).

Alternatively, the energy production device 50 may utilize a triboelectric generator that may be activated through application of an external magnetic field to magnetizable elements of the generator. An example of a triboelectric generator is presented by the 2012 Elsevier Nano Energy online article by F-R Fan, entitled "Flexible triboelectric generator!", in volume 1, pages 328-334 (incorporated herein by reference in its entirety).

Alternatively the energy production device may utilize a piezoelectric generator that may be activated through application of an external magnetic field to magnetizable elements of the generator. An example of a small piezoelectric generator is described in the 2012 NanoLetters article by N Cui et al, entitled "Magnetic Force Driven Nanogenerators as a Noncontact Energy Harvester and Sensor" (incorporated herein by reference in its entirety).

Alternatively, the energy production device may utilize a variable capacitance-based generator that may be activated through application of an external magnetic field to magnetizable elements of the generator. An example of a small variable-capacitance generator is described in the 2003 IEEE article by J Boland et al, entitled "Micro Electret Power Generator" (incorporated herein by reference in its entirety).

A variable-capacitance generator works, in broad terms, by changing the capacitance of a capacitor that has been loaded with charge, and thereby generating current.

It should be understood that the STNO itself may be powered by energy harvesting from the externally-applied magnetic field, by variable magnetocapacitance principles. In this case, the capacitance of the device may be changed through the application of an external magnetic field, in order to yield a current.

Alternatively the external electromagnetic field may affect the local voltages, for example by adding to the local voltage through induction of an electric field from a changing externally applied magnetic field.

The invention may be used to sense local voltages and/or currents in order to report on the local physiology. For example, a neuron can exhibit a very high local electric field, due to voltages of hundreds of millivolts across a very thin membrane. In one embodiment of the present invention, the voltage or current sensed by the antenna is converted by an amplifier into a current that is delivered to the STNO in order to modulate the RF signal emitted by the STNO. Modulation of an RF signal from an input current is described in the 2013 article in Scientific Reports (volume 3, article 1426) by Z Zeng et al, entitled "Ultralow-current-density and bias-field-free spin-transfer nano-oscillator" (incorporated herein by reference in its entirety).

It should be understood that the sensing function of the particle may actually be carried out by other electrical components or structures, for example a capacitive pickup circuit. It is understood that the sensing function may be generalized to include transduction of chemical concentration signals into electrical signals. An example of such transduction is described in the 2008 article by F Rock et al, entitled "Electronic Nose: Current Status and Future Trends", published in the journal Chem. Rev. volume 108 (2), pages 705-725 (incorporated herein by reference in its entirety).

Figure 3:
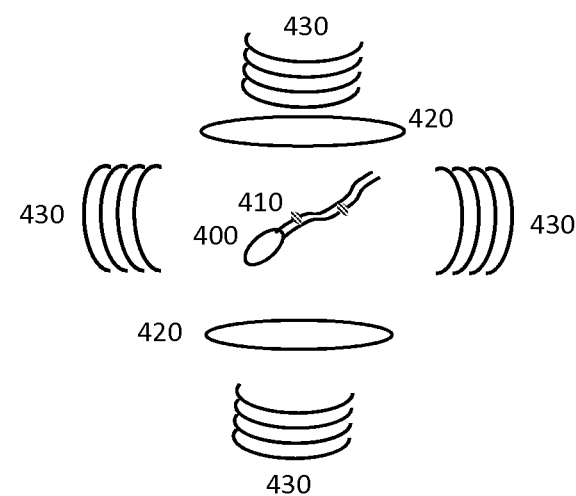
FIG. 3 illustrates one example of a configuration of provided by the disclosed embodiments wherein a neuron is in the vicinity of STNO particles.

The operation of the STNO may further be modulated through the application of a spatially and/or time varying magnetic field that is applied by an external generator. An example of an STNO that is sensitive to the local magnetic field is given in the 2010 article in the journal Nature Communications by A. Dussaux et al (volume 1, article 8) entitled "Large microwave generation from current-driven magnetic vortex oscillators in magnetic tunnel junctions" (incorporated herein by reference in its entirety). The configuration of the particle in the field is represented in FIG. 3, where neuron 400 is in the vicinity of STNO particles 410. RF emitted by particles 410 is detected by coil 420. A magnetic gradient which affects the frequency of RF signals emitted by 410 is created with coils 430.

Thus, the particle may be responsive to factors in the environment in which it resides, which may be due to local events (for example, neuronal voltages, the presence of a chemical, etc.) or externally applied events (for example, magnetic gradients). It is understood that the application of external gradients can be used to realize an image of the particles, and also of the particles that have been activated by neurons or other local factors. It is understood that the presence of a chemical may be sensed by the particle through the use of a generalized antenna as described above.

Figure 4:
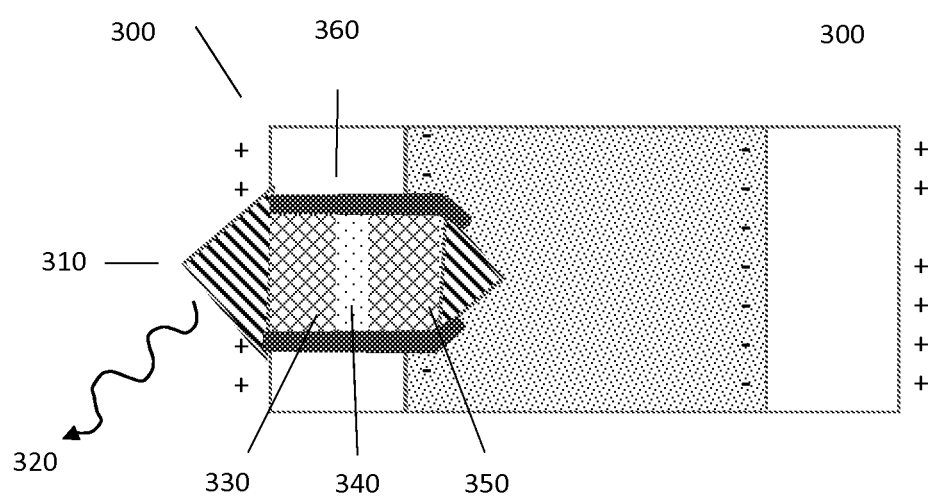
FIG. 4 illustrates one example of selective orientation of an STNO particle straddling a polarized neuronal membrane.

The particle may be coated with some material or process so the particle is oriented preferentially with respect to the assembly of nerves in the tissue, for example in order to maximize signal received outside the body by a receiver. For example, the particle may straddle the nerve membrane, as illustrated in FIG. 4, in order to maximize the electrical potential sensed by the particle. As an example of such coating pattern, the particle may be coated with a hydrophobic region flanked by two hydrophilic regions, so as to form a stable configuration along a cell membrane. An example of selective orientation is shown in FIG. 4, representing an STNO particle traversing the polarized neuronal membrane 300. The STNO is shown with a conducting electrode cap 310, and is emitting RF energy 320. Parts of a typical STNO are represented in this figure, including oscillating magnetic layer 330, tunnel barrier 340, pinned magnetic layer 350. Particle is coated with lipophilic insulator 360 in order to maintain its position straddling the neuronal membrane 300.

It should be understood that the particle may be transported in the body using magnetic gradients and fields, as described in prior provisional patent application by Weinberg, entitled "Neuroparticle", assigned with application No. 61/810,436, and as in provisional patent application by Weinberg, entitled "System, Method and Equipment for Implementing Temporary Diamagnetic Propulsion with Transient Applied Magnetic Field Pulses", assigned with application Ser. No. 14/182,488, and with inventions described in those patent applications (both incorporated herein by reference in their entirety).

As in those prior inventions, the particle may affect its local environment through emission of an electrical current or voltage or heat or light or release of a chemical, in response to a change in its local environment, said change resulting from locally-occurring electromagnetic or chemical factors and/or from electromagnetic factors caused by a generator outside the body.

Disclosed embodiments may be utilized to stimulate or otherwise affect portions of the nervous system of a subject's body without affecting other portions of the nervous system, depending on the local environment sensed by the particle. The presently disclosed embodiments apply the principle of selecting zones magnetically to specify spatial locations in which very small circuits can be selectively activated or deactivated, in which the selection may depend on the local environment sensed by the particle, and which once activated may stimulate, affect, and/or sense nearby tissues.

Although the term "stimulate" is used as an illustration of the mechanism for increasing the firing rate of neurons, it should be understood that the disclosed embodiments may also be used to decrease the firing rate of neurons (i.e., inhibit firing) by repeatedly stimulating neurons (e.g., by depleting stores of neurotransmitters) or by shorting electrical circuitry in neurons, or by heating nearby tissues, or electroporating nearby tissues, or through other neurophysiological means.

It should be understood that the effect on nearby tissues may be destructive, as would be desirable if the tissues were malignant or causing epilepsy or tremors to occur. In such a situation, the tissues affected might be other than neuronal tissues. The destruction could be immediate, or could result in long-term damage as might affect the ability of the cells to reproduce, or could potentiate other means of affecting tissues (e.g., by sensitizing tissue to subsequent radiation therapy).

In accordance with at least one disclosed embodiment, an apparatus and method may be provided for spatially-selective administration of actions by at least one device in the body using a transducer that is sensitive to a spatially-variant energy field imposed on the at least one device by a source external to a subject's body, as disclosed in U.S. Provisional patent application Ser. No. 14/221,777, incorporated by reference herein.

In accordance with at least one disclosed embodiment, at least one component in the at least one device, wherein interaction of the transducer with the imposed spatially-variant energy field causes or enables at least one component in the at least one device to affect nearby tissues in the body.

Thus, disclosed embodiments may be utilized to stimulate or otherwise affect portions of the nervous system of a subject's body without affecting other portions of the nervous system.

It should be understood that the effect on nearby tissues may be destructive, as would be desirable if the tissues were malignant or causing epilepsy or tremors to occur. In such a situation, the tissues affected might be other than neuronal tissues. The destruction could be immediate, or could result in long-term damage as might affect the ability of the cells to reproduce, or could potentiate other means of affecting tissues (e.g., by sensitizing tissue to subsequent radiation therapy).

It should be understood that the above-disclosed embodiments and constituent equipment may be coupled to a computer processor that may be configured to output the image data and/or one or more graphical or image representations of that data to memory for storage and further analysis or reference at a later date. Further, the software code, instructions and algorithms utilized may be utilized by such a processor and may be stored in a memory that may include any type of known memory device including any mechanism for storing computer executable instructions and data used by a processor. Further, the memory may be implemented with any combination of read only memory modules or random access memory modules, optionally including both volatile and nonvolatile memory. Alternatively, some or all of the device computer executable instructions may be embodied in hardware or firmware (not illustrated). Further, it should be appreciated that, although not illustrated, the apparatus may similarly be coupled for communication and control to one or more user interfaces that may include display screens, one or more keyboards, and other types of user interface equipment.

It should be understood that the assembly of particles, once introduced into the body, may be considered as a contrast agent from the point of view of diagnostic imaging, in which the degree of contrast may depend on the local environment sensed by the assembly of particles. As described above in the publication by Kaka et al, some or all of the assembly of particles can operate coherently in order to effectively boost the signal received outside the body.

It should be understood that the invention can be applied within the nervous system and also in other tissues of the body.

While this invention has been described in conjunction with the specific embodiments outlined above, it is evident that many alternatives, modifications and variations will be apparent to those skilled in the art. Accordingly, the various embodiments of the invention, as set forth above, are intended to be illustrative, not limiting. Various changes may be made without departing from the spirit and scope of the invention.

It should be understood that the functionality described in connection with various described components of various invention embodiments may be combined or separated from one another in such a way that the architecture of the invention is somewhat different than what is expressly disclosed herein. Moreover, it should be understood that, unless otherwise specified, there is no essential requirement that methodology operations be performed in the illustrated order; therefore, one of ordinary skill in the art would recognize that some operations may be performed in one or more alternative order and/or simultaneously.

Further, it should be understood that, in accordance with at least one embodiment of the invention, system components may be implemented together or separately and there may be one or more of any or all of the disclosed system components. Further, system components may be either dedicated systems or such functionality may be implemented as virtual systems implemented on general purpose equipment via software implementations.

As a result, it will be apparent for those skilled in the art that the illustrative embodiments described are only examples and that various modifications can be made within the scope of the invention as defined in the appended claims.

What is claimed is:

1. An apparatus for monitoring an environment in a subject's body, the apparatus comprising:
    at least one particle, introduced into the subject's body, the at least one particle including at least one spin torque nano-oscillator; and
    at least one receiver located outside the subject's body, wherein the receiver is sensitive to radiation emitted by the at least one spin torque nano-oscillator of the at least one particle.

2. The apparatus of claim 1, further comprising at least one generator located outside the subject's body, the at least one generator generating a spatially-variant magnetic field.

3. The apparatus of claim 2, where the radiation emission depends at least in part on a local environment within the subject's body in which the at least one particle is located.

4. The apparatus of claim 2, wherein a local environment within the subject's body in which the at least one particle is located is affected at least in part by the at least one generator.

5. The apparatus of claim 1, further comprising at least one generator that affects a local electromagnetic environment of the subject's body.

6. The apparatus of claim 5, wherein the at least one particle is powered by the at least one generator.

7. The apparatus of claim 5, wherein the at least one generator is a fuel cell.

8. The apparatus of claim 5, wherein the at least one generator is a tribological generator.

9. The apparatus of claim 5, wherein the at least one generator is a piezoelectric generator.

10. The apparatus of claim 5, wherein the at least one generator is a variable capacitance generator.

11. The apparatus of claim 5, where the local environment affected at least in part due to neuronal activity.

12. The apparatus of claim 1, wherein the at least one particle contains magnetizable material.

13. The apparatus of claim 1, further comprising at least one generator located outside of the subject's body, the at least one generator creating electromagnetic fields that are controlled to transport the at least one particle in the subject's body.

14. The apparatus of claim 1, wherein a spatial distribution of the at least one particle is indicated by a response of the at least one particle to electromagnetic gradients created by at least one generator located outside the subject's body.

15. The apparatus of claim 1, wherein a spatial distribution and state of the at least one particle is indicated by a response of the at least one particle to electromagnetic gradients created by at least one generator located outside the subject's body and by a response of the at least one particle to the local environment.

16. The apparatus of claim 1, wherein the at least one particle influences a local environment in which the at least one particle is located as a result of a change in the local environment.

17. The apparatus of claim 1, wherein the at least one particle is oriented preferentially as a result of coatings.

18. The apparatus of claim 1, wherein current from a one or more nerves in electrical contact with the at least one particle is compressed to apply a shorter and stronger current to the spin torque nano-oscillator.

19. The apparatus of claim 1, wherein assemblies of spin torque nano-oscillators fire synchronously to boost a signal received by the at least one receiver outside the body.

20. The apparatus of claim 1, wherein a frequency of the signal emitted by the spin torque nano-oscillator is influenced by an electromagnetic field applied with an external generator, and a threshold for signal emission is influenced by local milieu of the spin torque nano-oscillator.

21. The apparatus of claim 20, wherein the threshold for emission by the spin torque nano-oscillator is influenced by both the electromagnetic field applied with the external generator, and a local milieu of the spin torque nano-oscillator.

22. A method for imaging neural activity in a subject's body using at least one particle with a spin torque nano-oscillator that emits electromagnetic radiation, the method comprising:
    transporting at least one particle into or within the subject's body;
    applying electromagnetic gradients to the at least one particle by at least one generator located outside the subject's body,
    wherein the electromagnetic radiation emitted by the spin torque nano-oscillator is sensitive to electromagnetic aspects of a local environment associated with neural activity and is sensitive to electromagnetic gradients applied by the one or more generators external to the body, and
    detecting the electromagnetic radiation emitted and generating an image based on the detected radiation,
    wherein a spatial distribution of the at least one particle is indicated by a response of the at least one particle to electromagnetic gradients created by at least one generator located outside the subject's body.

23. The method of claim 22, further comprising generating, using at least one generator located outside the subject's body, a spatially-variant magnetic field.

24. The method of claim 23, where the radiation emission depends at least in part on a local environment within the subject's body in which the at least one particle is located.

25. The method of claim 23, wherein a local environment within the subject's body in which the at least one particle is located is affected at least in part by the at least one generator.

26. The method of claim 22, further comprising at least one generator that affects a local electromagnetic environment of the subject's body.

27. The method of claim 26, wherein the at least one particle is powered by the at least one generator.

28. The method of claim 26, wherein the at least one generator is a fuel cell.

29. The method of claim 26, wherein the at least one generator is a tribological generator.

30. The method of claim 26, wherein the at least one generator is a piezoelectric generator.

31. The method of claim 26, wherein the at least one generator is a variable capacitance generator.

32. The method of claim 26, where the local environment affected at least in part due to neuronal activity.

33. The method of claim 22, wherein the at least one particle contains magnetizable material.

34. The method of claim 22, further comprising creating electromagnetic fields using at least one generator located outside of the subject's body, the at least one generator creating electromagnetic fields that are controlled to transport the at least one particle in the subject's body.

35. The method of claim 22, wherein a state of the at least one particle is indicated by a response of the at least one particle to electromagnetic gradients created by at least one generator located outside the subject's body and by a response of the at least one particle to the local environment.

36. The method of claim 22, wherein the at least one particle influences a local environment in which the at least one particle is located as a result of a change in the local environment.

37. The method of claim 22, wherein the at least one particle is oriented preferentially as a result of coatings.

38. The method of claim 22, wherein current from a milieu in which the at least one particle is located is compressed to apply a shorter and stronger current to the spin torque nano-oscillator.

39. The method of claim 22, wherein assemblies of spin torque nano-oscillators fire synchronously to boost a signal received by the at least one receiver outside the body.

40. The method of claim 22, wherein a frequency of the signal emitted by the spin torque nano-oscillator is influenced by an electromagnetic field applied with the external generator, and a threshold for signal emission is influenced by a local milieu of the spin torque nano-oscillator.

41. The method of claim 40, wherein the threshold for emission by the spin torque nano-oscillator is influenced by both the electromagnetic field applied with the external generator, and a local environment of the spin torque nano-oscillator.

* * * * *